United States Patent [19]

Shreve et al.

[11] Patent Number: 4,522,919
[45] Date of Patent: Jun. 11, 1985

[54] METHOD OF PRODUCING ANTIBACTERIAL AGENTS AND BIOCONVERTING MICROORGANISM THEREFOR

[75] Inventors: Barbara B. Shreve, Indianapolis; Jan R. Turner, Carmel, both of Ind.

[73] Assignee: Eli Lilly and Company, Indianapolis, Ind.

[21] Appl. No.: 471,928

[22] Filed: Mar. 3, 1983

[51] Int. Cl.³ .................. C12P 17/18; C12R 1/465
[52] U.S. Cl. ............................. 435/119; 435/253; 435/886
[58] Field of Search .................. 435/119, 253, 886

[56] References Cited

U.S. PATENT DOCUMENTS 3,326,759 6/1967 Hamill et al. .................. 167/65
4,092,473 5/1978 Okamoto et al. ............. 536/17
4,205,163 5/1980 Mori et al. .................... 536/17 R
4,385,116 5/1983 Baltz et al. .................... 435/76

OTHER PUBLICATIONS

Sebek et al., Genetics of Industrial Microorganisms, Pub. by American Society for Microbiology, pp. 117-122 (1979).
M. Tsuchiya et al., "Studies on the Effects of 3-Acetyl-4"-Isovaleryltylosin Against Multiple-Drug Resistant Strains of Staphylococcus Aureus", J. Antibiotics 34(3), 305-306 (1981).
M. Tsuchiya et al., "Studies of Tylosin Derivatives Effective Against Macrolide-Resistant Strains: Synthesis and Structure-Activity Relationships", J. Antibiotics 35(6), 661-671 (1982).
Derwent Abstract Nos. 66634C/38, 27592A/15 of Japanese Unexamined Patent Nos. J5 5043-013, J5 3021-182, 3-26-80, 2-27-78 (Sanraku Ocean).
Okamoto et al., "The Activity of 4"-Acylated Tylosin Derivatives Against Macrolide-Resistant Gram-Positive Bacteria: J. Antibiotics 32, 542-544 (1979).
Okamoto et al., "Biological Properties of New Acyl Derivatives of Tylosin", J. Antibiotics 33, 1309-1315 (1980).

Primary Examiner—Alvin E. Tanenholtz
Attorney, Agent, or Firm—Nancy J. Harrison; Arthur R. Whale

[57] ABSTRACT

Improved bioconverting strain of Streptomyces thermotolerans useful in preparing tylosin esters and new antibacterial macrocin or lactenocin ester derivatives of the formula:

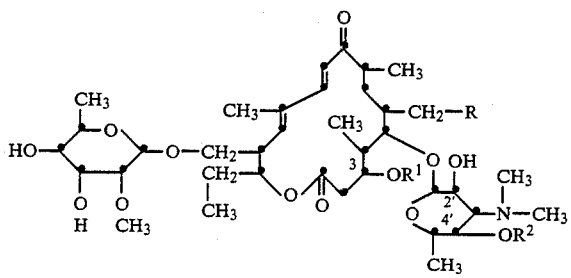

wherein R is formyl or hydroxymethyl; $R^1$ is hydrogen, acetyl or propionyl; $R^2$ is hydrogen or

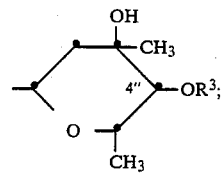

and $R^3$ is hydrogen, acetyl, propionyl, n-butyryl or isovaleryl; provided that one of $R^1$ or $R^3$ must be other than hydrogen.

4 Claims, No Drawings

METHOD OF PRODUCING ANTIBACTERIAL AGENTS AND BIOCONVERTING MICROORGANISM THEREFOR

SUMMARY OF THE INVENTION

This invention provides a new strain of *Streptomyces thermotolerans* which has improved characteristics useful in the preparation of certain tylosin esters and in the preparation of macrocin and lactenocin derivatives having formula 1:

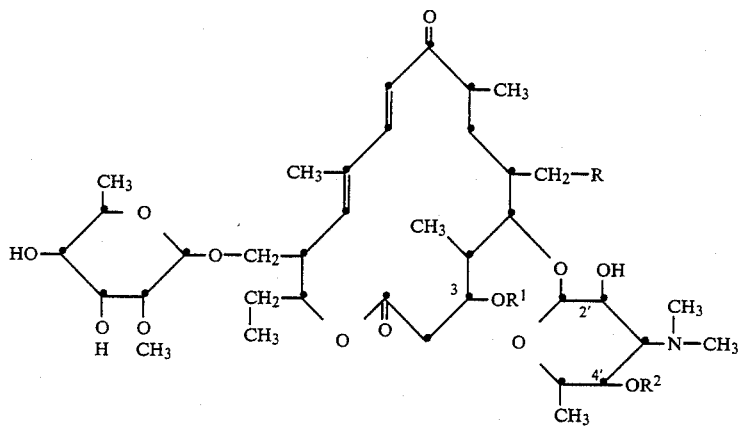

wherein R is formyl or hydroxymethyl; $R^1$ is hydrogen, acetyl or propionyl; $R^2$ is hydrogen or

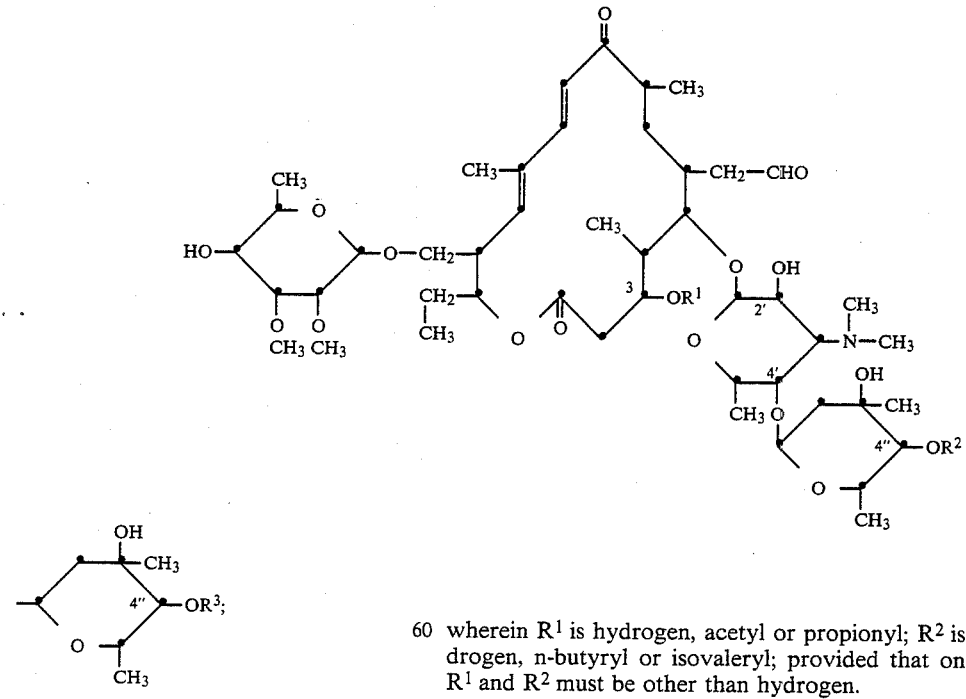

and $R^3$ is hydrogen, acetyl, propionyl, n-butyryl or isovaleryl; provided that one of $R^1$ or $R^3$ must be other than hydrogen.

The compounds prepared using the microorganism of this invention are useful antibacterial agents. The formula 1 compounds are also useful in the treatment of Mycoplasma infections.

DETAILED DESCRIPTION OF THE INVENTION

We have discovered an improved *Streptomyces thermotolerans* strain which is useful in certain bioconversion reactions. More particularly, the *Streptomyces thermotolerans* strain of this invention has an improved ability to acylate macrocin and lactenocin to give the derivatives of formula 1. Furthermore, the *S. thermotolerans* strain of this invention has an improved ability to acylate tylosin to produce the tylosin derivatives described by R. Okamoto et al. in U.S. Pat. No. 4,092,473. Thus, this invention provides an improved process for preparing compounds of the formula wherein $R^1$ is hydrogen, acetyl or propionyl; $R^2$ is hydrogen, n-butyryl or isovaleryl; provided that one of $R^1$ and $R^2$ must be other than hydrogen.

The *S. thermotolerans* strain of this invention is superior in several ways to the *S. thermotolerans* ATCC 11416 strain from which it was developed. The most important trait of the strain of this invention is its improved ability to acylate macrocin, lactenocin and tylosin to give useful compounds.

The improved bioconverting strain of this invention was discovered among a group of 522 mutant strains of *Streptomyces thermotolerans* ATCC 11416. From this group of mutants, 192 were tested for their ability to acylate a macrolide antibiotic. Based on this study, 22 cultures were selected as superior in their ability to acylate the antibiotic. Of these, seven were chosen on the basis of favorable traits and tested further. The strain of the present invention was discovered among this group. When compared with both the parent culture and with the other selected mutants, the *S. thermotolerans* strain of this invention was superior to all in its ability to acylate the macrolide antibiotic at the 3- and 4"-positions. The new strain acylates the antibiotic more rapidly, giving better yields of the product derivative. In addition, the new strain provides consistent acylation, whereas the parent strain is erratic in its ability to acylate.

The *Streptomyces thermotolerans* strain of this invention has been deposited and made part of the stock culture collection of the Northern Regional Research Center, Agricultural Research, North Central Region, 1815 North University Street, Peoria, Ill., 61604, from which it is available to the public under the accession number NRRL 15270.

As is true with other organisms, the characeristics of *Streptomyces thermotolerans* NRRL 15270 are subject to variation. For example, recombinants, mutants or artificial variants of the NRRL 15270 strain may be obtained by treatment with various known physical and chemical mutagens, such as ultraviolet light, X-rays, gamma rays, and N-methyl-N'-nitro-N-nitrosoguanidine. All natural and artificial variants, mutants and recombinants of *Streptomyces thermotolerans* NRRL 15270 which retain its improved ability to acylate macrocin, lactenocin and tylosin may be used in this invention.

The formula 1 compounds were discovered by Jan R. Turner, Veronica M. Krupinski, David S. Fukuda and Richard H. Baltz and are described in their copending application entitled Macrocin Derivatives and Process for Their Preparation, Ser. No. 471,628, filed herewith this even date. The formula 1 compounds can be prepared by contacting macrocin or lactenocin with an acyl donor in the presence of the acylating enzyme system from the *S. thermotolerans* strain of this invention. The enzyme system can be in the form of cells or enzyme preparations.

The compounds of formula 1 wherein R is formyl are prepared initially in the bioconversion reaction. The compounds of formula 1 wherein R is hydroxymethyl, which are called the "C-20-dihydro" compounds, are prepared by reduction, either chemical or biochemical, of the formula 1 compounds wherein R is formyl.

The compounds of formula 1 wherein $R^2$ is

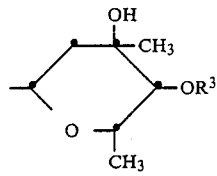

are prepared when macrocin is used as the substrate in the bioconversion.

The compounds of formula 1 wherein $R^2$ is hydrogen can be prepared by using lactenocin in the bioconverting reaction.

In order to illustrate more fully the operation of this invention, the following examples are provided:

EXAMPLE 1

Bioconversion of Macrocin to 3-O-Acetylmacrocin, 3-O-Acetyl-4"-O-(n-Butyryl)macrocin and 3-O-Acetyl-4"-O-Isovalerylmacrocin by *Streptomyces thermotolerans* NRRL 15270

A. Inoculum Preparation

Suitable vegetative inoculum may be obtained by inoculating sterilized medium with lyophilized spore suspensions or spore suspensions obtained by scraping spores from a well sporulated slant of *Streptomyces thermotolerans* NRRL 15270; best results, however, have been obtained using cultures inoculated from a standardized vegetative inoculum that has been preserved in liquid nitrogen. Liquid-nitrogen-stock inoculum is prepared in the following manner:

A lyophilized stock of *S. thermotolerans* NRRL 15270 is suspended in sterile water (2 ml). The resulting spore suspension is inoculated into 50 ml of sterile medium in a 250-ml wide-mouth Erlenmeyer flask at a rate of 0.4% volume/volume (v/v). The medium has the following composition:

| Vegetative Medium Composition (CSI) | |
|---|---|
| Ingredient | Amount |
| Glucose | 25 g |
| Soybean grits | 15 g |
| Blackstrap molasses | 3 g |
| Enzyme-hydrolyzed casein[a] | 1 g |
| $CaCO_3$ | 2.5 g |
| Czapek's Mineral Stock[b] | 2 ml |
| Deionized $H_2O$ to a total of one liter pH adjusted to 7.2 prior to sterilization; autoclave 45 minutes | |

[a]Amber EHA (Amber Laboratories, Juneau, WI)
[b]Czapek's Mineral Stock
| KCl | 100 g |
| $MgSO_4.7H_2O$ | 100 g |
| Deionized Water | 900 ml |

$FeSO_4.7H_2O$ (2 g) was dissolved in 100 ml distilled water containing 2 ml of concentrated HCl. This solution was added to the above $KCl/MgSO_4.7H_2O$ solution to complete preparation of the Czapek's Minerals.

Flasks containing inoculated media are maintained at 37° C. on a rotary shaker agitating in a 2-inch-diameter arc at 260 RPM for 24 hours. The vegetative culture is then harvested, diluted 1:1 (volume:volume) with a sterile suspending agent of glycerol:lactose:water (2:1:7) and dispensed into sterile tubes (2 ml/tube). The diluted inoculum is then stored over liquid nitrogen in appropriate storage containers and used as a working-stock inoculum for the cultivation of shake-flask conversion cultures and fermenter seed inoculum.

B. General Shake-flask Conversion Procedure

Shake-flask conversions are generally conducted with a culture-volume to flask-volume ratio of 1/5. Sterilized CSI medium is inoculated with liquid-nitrogen-preserved stock inoculum at a rate of 0.4% v/v and incubated at 37° C. on a rotary shaker with a 2-inch-diameter arc at 260 RPM for 22-24 hours. A concentrated methanolic solution containing macrocin and a sterilized, neutralized solution containing DL-norvaline and L-leucine are then added to the converting culture at respective final concentrations of 0.5 mg macrocin/ml and 1.0 mg of each amino acid/ml. The culture is incubated an additional 24 hours as described supra and then is harvested. Conversion-products are recovered by adjusting the pH of the whole culture to about pH 8.5–9.0 and repeatedly extracting with equal volumes of ethyl acetate. Extracts are combined and concentrated under vacuum to dryness. The various conversion products are recovered in purified form via reversed-phase (RP) high performance liquid chromatography (HPLC).

In general, shake-flask conversions result in complete conversion of substrate to the corresponding 3-O-acetyl derivative in 8–10 hours, followed by subsequent conversion of the 3-O-acetyl intermediate to the 3-O-acetyl-4"-O-(n-butyryl) and/or 3-O-acetyl-4"-O-isovaleryl derivatives. Extension of the conversion time beyond 24–28-hours results in the partial conversion of products to the C-20 dihydro-derivative.

C. General Procedure for Conversion in Stirred Fermenters

Seed inoculum for stirred fermenters (tanks) is prepared by inoculating 200 ml of sterile CSI medium in a one-liter wide-mouth Erlenmyer flask with liquid-nitrogen-stock inoculum at a rate of 0.4% v/v. The seed culture is then incubated at 37° C. on a rotary shaker with a 2-inch diameter arc at 260 RPM for 22 hours. The resulting vegetative culture is used to inoculate a stirred fermenter containing 25 liters of sterile medium (0.8% inoculum, v/v) which has the following composition:

| Tank Fermentation Medium | |
|---|---|
| Ingredient | Amount |
| Antifoam agent[a] | 0.2 g |
| Glucose | 25 g |
| Soybean grits | 15 g |
| Blackstrap molasses | 3 g |
| Casein | 1 g |
| $CaCO_3$ | 5 g |
| Czapek's Mineral Stock | 2 ml |
| Deionized water q.s. to | 1 liter |

[a]Dow Corning (Chicago, IL)
Sterilize for 45 minutes at about 126° C. and 20–23 psi Fermentation temperature is maintained at 37°°C. Two 6-blade 6-inch-diameter impellers mounted on the fermenter impeller shaft are rotated at 300 RPM to provide agitation. The culture is aerated by sparging sterile air into the fermenter below the bottom impeller at a rate of 0.5 v/v/m. Sterilized, neutralized solutions (2 L.) containing DL-norvaline (25 g), L-leucine (25 g) and 50–100 ml of a solution of macrocin (12.5 g) in methanol are added to the culture after 22–24 hours of growth. Fermentation is continued for an additional 22–24 hours, although in most cases conversion is complete in 12–16 hours.

Macrocin is rapidly converted to 3-O-acetyl macrocin, usually within three hours after substrate addition. Conversion of 3-O-acetyl macrocin to the 3-O-acetyl-4"-O-(n-butyryl)macrocin and 3-O-acetyl-4"-O-isovalerylmacrocin derivatives occurs at a somewhat slower rate. Maximum 4"-ester formation usually occurs about 7–16 hours after substrate addition. When the converting culture is harvested about 7–8 hours after substrate addition, conversion to the 3,4"-diester is approximately 85–95% complete and formation of the C-20-dihydro products is minimized.

When preparing 3-O-acetyl-4"-O-isovalerylmacrocin, it is preferable to add L-leucine (50 g per 25 liters of culture) to the medium.

When C-20-dihydro compounds are desired, the fermentation is carried out for a longer period of time, preferably from about 22 to about 30 hours.

D. Assay Procedure

This assay method is useful for monitoring the bioconversion process and for isolating the individual bioconversion products: A sample (4 ml) of whole broth containing bioconversion product(s) is adjusted to pH 9.0 with NaOH and extracted once with ethyl acetate (2 ml). The resulting suspension is centrifuged, and the ethyl acetate portion is analyzed by reversed-phase HPLC, using Waters μ-Bondapak C-18 or Merck LiChrosorb RP-18 as the adsorbent. 3-O-Acetylmacrocin is assayed using the solvent system $H_2O$/MeOH/$NH_4COOH$ (40/60/0.2), while the 3,4"-diesters are assayed with the system $H_2O$/MeOH/$NH_4COOH$ (25/75/0.2). Macrocin and the ester derivatives are detected by ultraviolet (UV) absorption at 280 nm.

E. Isolation of Conversion Products

The pH of the fermentation broth is adjusted to about 8.5 with sodium hydroxide. Ethyl acetate (two volumes) is added with vigorous stirring. The resulting emulsion is passed through a Sepa centrifuge to sediment cellular debris and break the emulsion. Cell debris and the aqueous phase are discarded. The organic layer is concentrated under vacuum to an oily residue which is repeatedly triturated with hexane until an oil-free dry crude preparation is obtained. The yield of crude preparation is in the range of 3–9 g.

The crude dried preparation is subjected to repeated purification via reverse-phase HPLC until the appropriate derivative is obtained in pure form.

Initially, 3-O-acetylmacrocin is separated from the diesters by preparative HPLC (Waters Prep/500-reversed-phase) of crude dried extract (in amounts of about 3–7 g), using the solvent system $H_2O$/$CH_3CN$/diethylamine (65/35/0.1). Diesters are partially separated from each other using the system $H_2O$/$CH_3CN$/pyridine/HOAc (65/35/1.5/0.5). Appropriate fractions, as determined by UV at 280 nm and analytical HPLC, are combined, concentrated to the aqueous phase and lyophilized to yield dry preparations.

The mono- and diesters are further purified by HPLC with either 38"×½" or 25.5"×1" LP-1/$C_{18}$ columns with the appropriate solvent system:

| Compound | Solvent System | Ratio |
|---|---|---|
| 3-O—acetylmacrocin | $H_2O$/$CH_3CN$/$NH_4HCO_3$ | (70/30/0.001) |
| 3-O—acetyl-4"-O—(n-butyryl)macrocin and 3-O—acetyl-4"-O—isovalerylmacrocin | $H_2O$/$CH_3CN$/pyridine/HOAc | (70/30/1.5/0.5) |

Approximate yields

| I. Step | Amount[a] |
|---|---|
| 50-Liter conversion culture | 25 g Macrocin |
| ↓ | ↓ |
| Ethyl acetate extrac- | 12.8 g crude product |

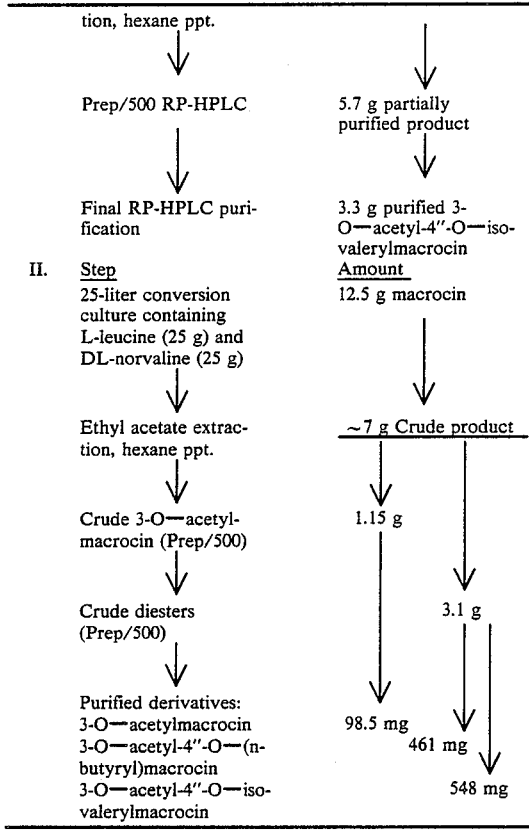

EXAMPLE 2

Acylating Ability of *Streptomyces thermotolerans* NRRL 15270 compared with that of *S. thermotolerans* ATCC 11416

The ability of *Streptomyces thermotolerans* ATCC 11416 and *S. thermotolerans* NRRL 15270 to esterify the macrolide antibiotics tylosin and macrocin at the 3'- and 4"-positions was compared. Vegetative cultures of each organism were prepared by inoculating sterilized CSI medium (medium to flask ratio 1:5) with lyophilized pellets of each organism. The cultures were incubated at 37° C. on a rotary shaker with a 2-inch diameter arc at 260 RPM for 24 hours. These cultures were used to inoculate fermentation broths of CSI medium at a rate of 0.4% volume/volume. The fermentation broths were incubated as described for the vegetative cultures for 24 hours. The fermentaton culture of each of the organisms was then divided equally into smaller flasks, maintaining a 1:5 medium-to-flask ratio. A concentrated solution of each compound (macrocin or tylosin) in methanol and a sterilized, neutralized solution of L-leucine were added to the duplicate fermentation cultures to give a final concentration of 0.5 mg/ml of macrosin or tylosin and 2 mg/ml of L-leucine. The cultures were incubated an additional 6 hours and then were harvested. Bioconversion products were isolated by adjusting the pH of the fermentation broths to 8.5 and extracting them twice with equal volumes of ethyl acetate. The ethyl acetate products were concentrated to dryness under vacuum and then reconstituted to half their fermentation volume with ethyl acetate. The extracts were examined by thin-layer chromatography (TLC) and HPLC. The TLC assay used silica-gel plates developed in ethyl acetate/diethylamine/methanol (95/5/10); detection of spots was made by shortwave UV and by anisaldehyde spray. The reversed-phase HPLC system used a Waters $\mu$-Bondapak $C_{18}$ column, a $H_2O$/MeOH/$NH_4COOH$ (25/75/0.2). solvent system, and UV detection at 280 nm.

Measured by both TLC and HPLC, the *Streptomyces thermotolerans* 15270 culture converted sigificantly more macrocin and thylosin to their respective 3-O-acyl-4"-O-acyl esters than did the *S. thermotolerans* ATCC 11416 culture. Comparison by TLC shows noticeable differences in intensity, the spot resulting from the experiment with *S. thermotolerans* NRRL 15270 being much darker than that from the *S. thermotolerans* ATCC 11416 culture. Comparison of HPLC peak heights measuring amounts of 3-O-acetyl-4"-isovaleryl macrocin and 3-O-acetyl-4"-O-isovaleryl tylosin produced indicated that the *S. thermotolerans* NRRL 15270 provided a significant increase in acylation when compared to that provided by *S. thermotolerans* ATCC 11416. The HPLC peak heights (in mm) attributable to the esterified compounds are as follows:

| Compound | HPLC Peak Heights (mm) | |
|---|---|---|
| | *S. thermotolerans* ATCC 11416 | *S. thermotolerans* NRRL 15270 |
| 3-O—Acetyl-4"-Iso-valerylmacrocin | 5 | 42 |
| | 6 | 48 |
| 3-O—Acetyl-4"-Iso-valeryltylosin | 3 | 24 |
| | 4 | 33 |

We claim:

1. A biologically purified culture of the microorganism *Streptomyces thermotolerans* NRRL 15270 or a mutant, variant or recombinant thereof which retains its improved ability to acylate macrocin, lactenocin and tylosin.

2. The culture of claim 1 wherein the microorganism is *Streptomyces thermotolerans* NRRL 15270.

3. A method of producing a compound of the formula

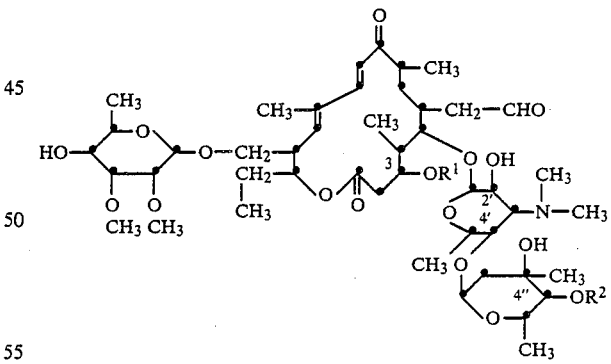

wherein $R^1$ is hydrogen, acetyl or propionyl;

$R^2$ is hydrogen, n-butyryl or isovaleryl;

provided that one of $R^1$ or $R^2$ must be other than hydrogen, which comprises contacting tolysin with an acyl donor in the presence of an acylating enazyme system from that produced by *Streptomyces thermotolerans* NRRL 15270 in an aqueous medium until a substantial amount of the compound is produced.

4. The method of claim 3 wherein the enzyme system is present in the culture medium in which it is produced.

* * * * *